(12) United States Patent
Ritland

(10) Patent No.: US 6,951,538 B2
(45) Date of Patent: Oct. 4, 2005

(54) RETRACTOR AND METHOD FOR SPINAL PEDICLE SCREW PLACEMENT

(75) Inventor: Stephen Ritland, Flagstaff, AZ (US)

(73) Assignee: DePuy Spine, Inc., Raynham, MA (US)

( * ) Notice: Subject to any disclaimer, the term of this patent is extended or adjusted under 35 U.S.C. 154(b) by 125 days.

(21) Appl. No.: 10/060,905

(22) Filed: Jan. 29, 2002

(65) Prior Publication Data

US 2002/0123668 A1 Sep. 5, 2002

Related U.S. Application Data

(60) Provisional application No. 60/264,943, filed on Jan. 29, 2001.

(51) Int. Cl.$^7$ .............................. A61B 1/04; A61B 17/90
(52) U.S. Cl. ............................ 600/210; 606/96; 606/97
(58) Field of Search ................................ 600/201, 205, 600/217, 210; 606/96, 97, 99

(56) References Cited

U.S. PATENT DOCUMENTS

| 4,232,660 | A | * | 11/1980 | Coles | |
|---|---|---|---|---|---|
| 4,481,947 | A | | 11/1984 | Chester | 128/303 |
| 4,617,922 | A | | 10/1986 | Griggs | 128/92 YS |
| 4,686,972 | A | * | 8/1987 | Kurland | |
| 4,747,394 | A | | 5/1988 | Watanabe | 128/20 |
| 4,817,587 | A | | 4/1989 | Janese | 128/20 |
| 5,035,232 | A | | 7/1991 | Lutze et al. | 128/20 |
| 5,052,373 | A | | 10/1991 | Michelson | 128/20 |
| 5,133,720 | A | * | 7/1992 | Greenberg | 606/96 |
| 5,303,694 | A | | 4/1994 | Mikhail | 128/20 |
| 5,363,841 | A | | 11/1994 | Coker | 128/20 |
| D361,381 | S | | 8/1995 | Koros et al. | D24/135 |
| 5,512,038 | A | | 4/1996 | O'Neal et al. | 600/210 |
| 5,601,550 | A | | 2/1997 | Esser | 606/54 |
| 5,716,415 | A | | 2/1998 | Steffee | 623/17 |
| 5,743,853 | A | | 4/1998 | Lauderdale | |
| 5,766,221 | A | | 6/1998 | Benderev et al. | 606/232 |
| D399,955 | S | | 10/1998 | Koros et al. | D24/135 |
| RE36,020 | E | * | 12/1998 | Moore et al. | 606/144 |
| 5,885,300 | A | | 3/1999 | Tokuhashi et al. | 606/99 |
| 5,891,147 | A | | 4/1999 | Moskovitz et al. | 606/79 |
| 5,895,352 | A | | 4/1999 | Kleiner | 600/206 |
| 5,895,390 | A | | 4/1999 | Moran et al. | 606/96 |
| 5,897,593 | A | | 4/1999 | Kohrs et al. | 623/17 |
| 5,913,818 | A | * | 6/1999 | Co et al. | 600/204 |
| 5,928,139 | A | * | 7/1999 | Koros et al. | 600/205 |
| 5,944,658 | A | | 8/1999 | Koros et al. | 600/232 |
| 6,007,487 | A | * | 12/1999 | Foley et al. | 600/235 |
| 6,063,088 | A | | 5/2000 | Winslow | 606/61 |
| 6,080,155 | A | | 6/2000 | Michelson | 606/61 |
| 6,083,225 | A | | 7/2000 | Winslow et al. | 606/61 |
| 6,113,602 | A | | 9/2000 | Sand | 606/61 |
| 6,120,506 | A | | 9/2000 | Kohrs et al. | 606/80 |

(Continued)

OTHER PUBLICATIONS

Wiltse, New Uses and Refinements of the Paraspinal Approach to the Lumbar Spine, Spine, vol. 13 No. 6 1988, pp. 696–706.

Web pages, http://www.brainlab.com, Apr. 2, 2002.

*Primary Examiner*—Cary E. O'Connor
(74) *Attorney, Agent, or Firm*—Nutter, McClennen & Fish LLP

(57) ABSTRACT

To avoid traditional muscle dissection required in the placement of a screw for a pedicle screw fixation, a retractor is provided having a guide of an appropriate length to provide access from the skin surface to the dorsal aspect of the vertebra over the pedicle. The retractor has a handle to provide appropriate holding leverage and to maintain the guide so as to stabilize the guide against the lateral aspects of the facet with the paraspinous musculature. The retractor has a channel of an appropriate size to accommodate a variety of tools, including a drill bit or a tap. The channel also provides a pathway for a probe or feeler to inspect the placement of the screw.

31 Claims, 3 Drawing Sheets

U.S. PATENT DOCUMENTS

| | | |
|---|---|---|
| 6,206,826 B1 | 3/2001 | Mathews et al. ............ 600/210 |
| 6,206,885 B1 | 3/2001 | Ghahremani et al. ......... 606/96 |
| 6,245,072 B1 | 6/2001 | Zdeblick et al. .............. 606/61 |
| 6,267,763 B1 | 7/2001 | Castro ......................... 606/61 |
| 6,270,498 B1 | 8/2001 | Michelson ................... 606/61 |
| 6,296,609 B1 | 10/2001 | Brau |
| 6,348,058 B1 * | 2/2002 | Melkent et al. .............. 606/130 |
| 6,428,472 B1 | 8/2002 | Haas .......................... 600/206 |
| 6,692,434 B2 | 2/2004 | Ritland |
| 2003/0220689 A1 | 11/2003 | Ritland et al. |
| 2003/0236447 A1 | 12/2003 | Ritland |

* cited by examiner

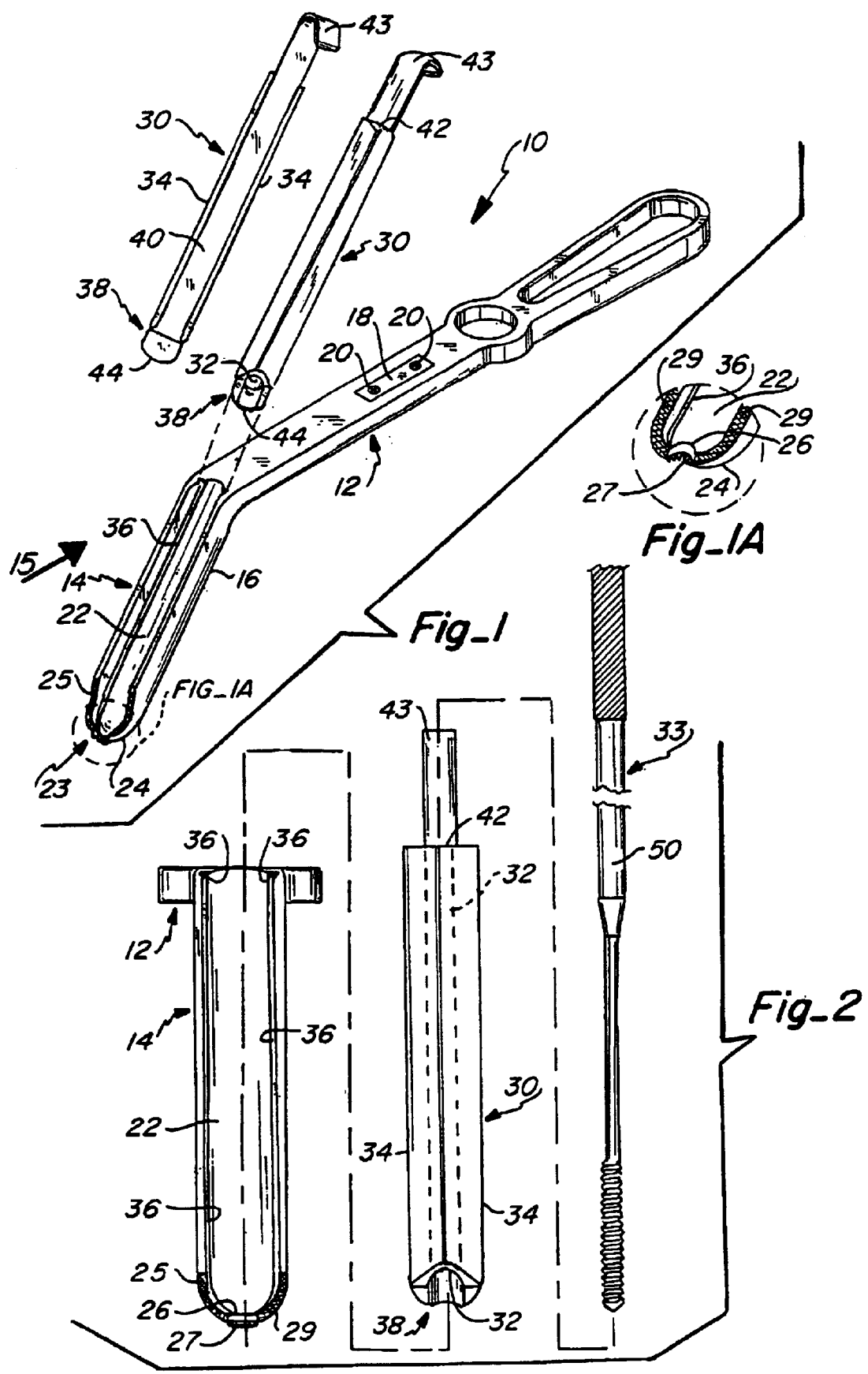

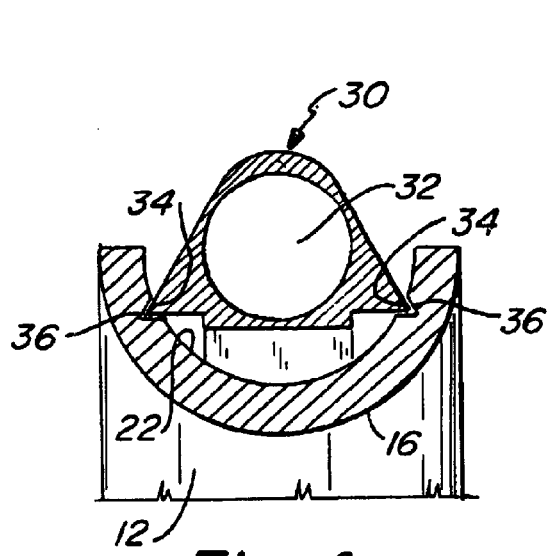
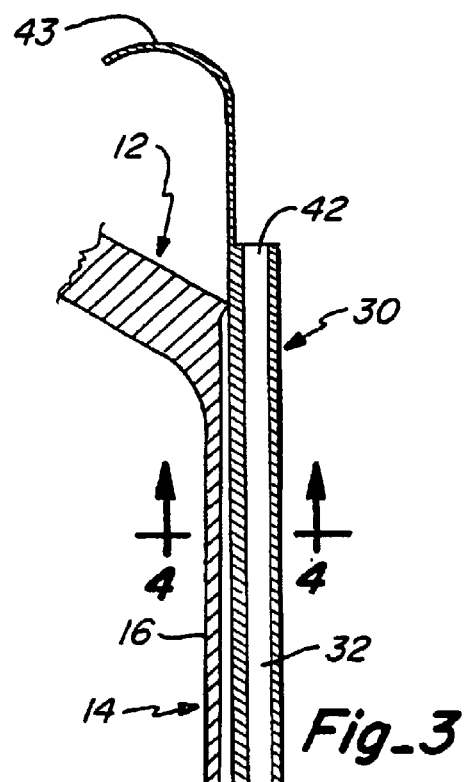
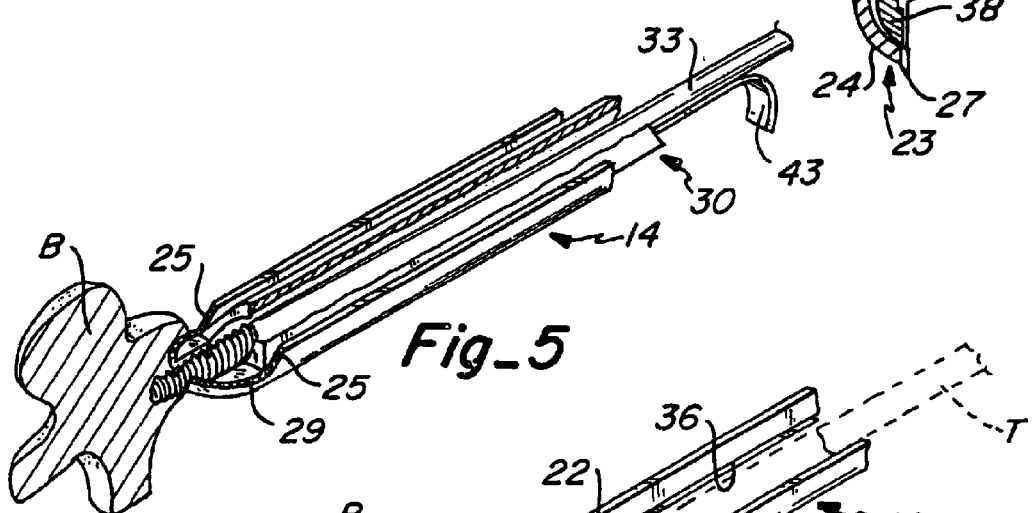
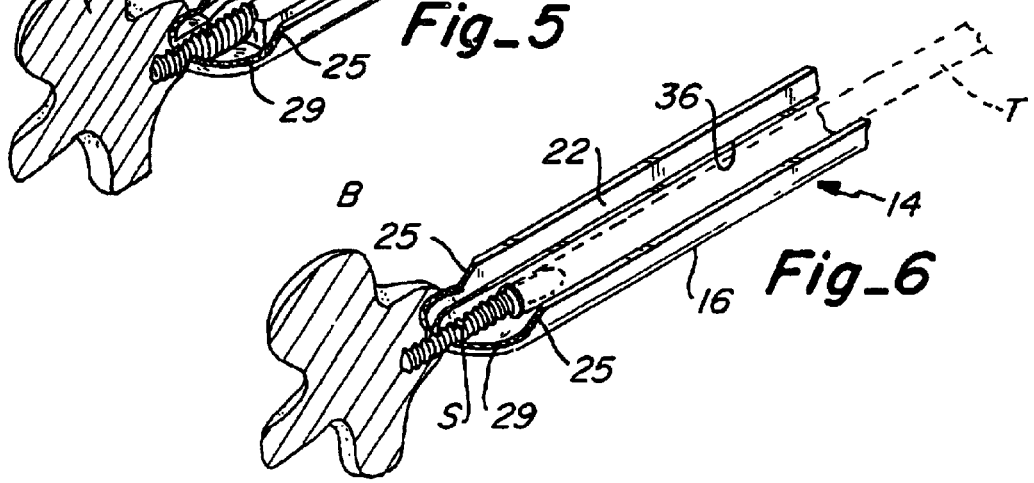

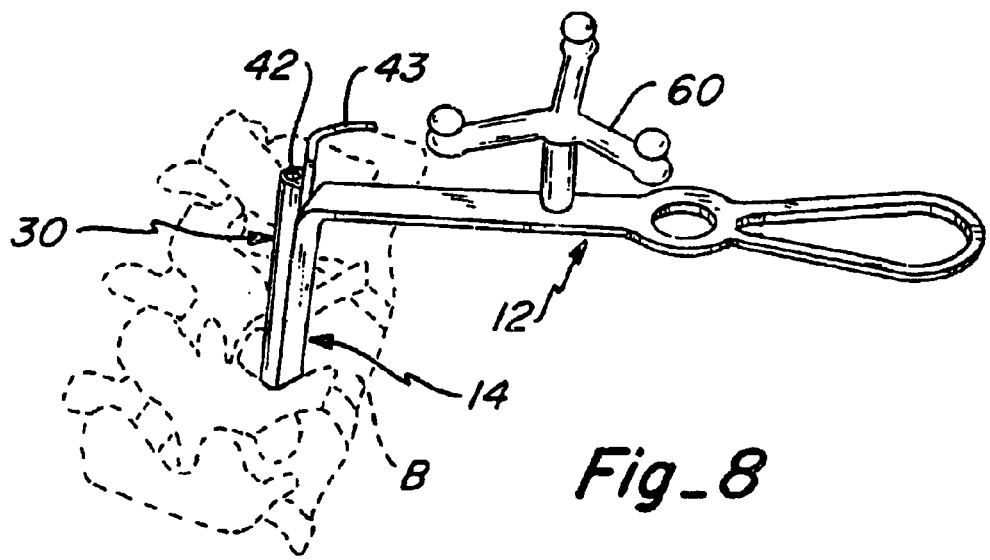
Fig_8
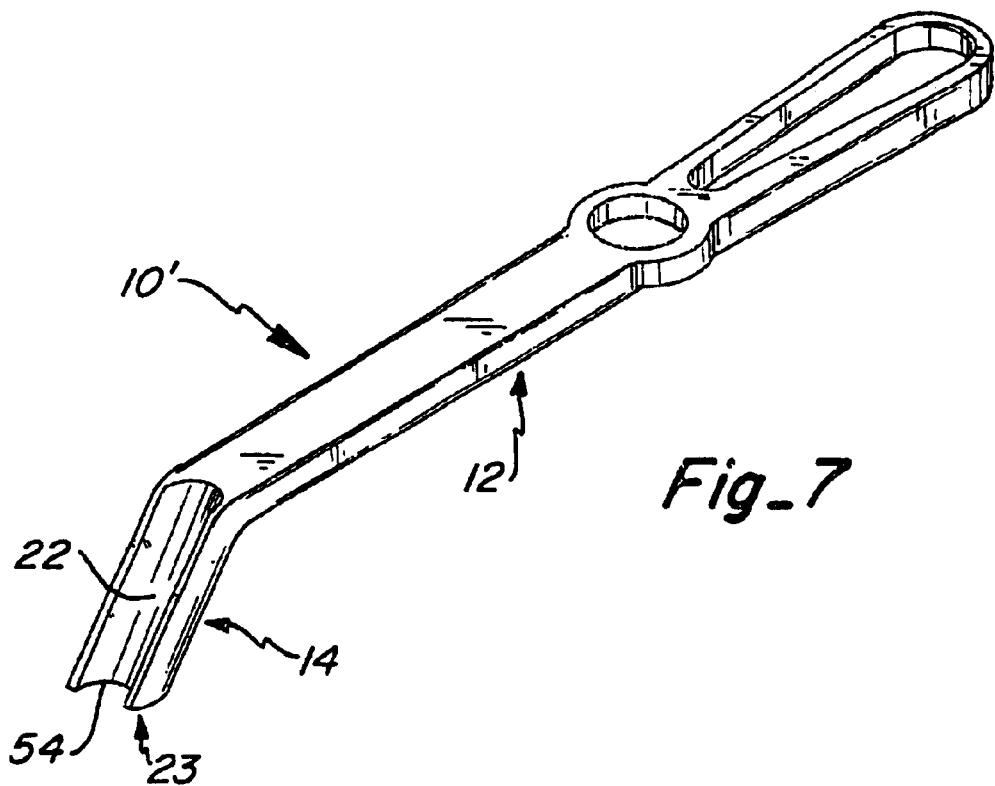
Fig_7

RETRACTOR AND METHOD FOR SPINAL PEDICLE SCREW PLACEMENT

CROSS-REFERENCE TO RELATED APPLICATIONS

Priority is claimed from U.S. Provisional Patent Application No. 60/264,943 filed Jan. 29, 2001 entitled "Retractor And Method For Spinal Pedicle Screw Placement," which is incorporated by reference in its entirety.

FIELD OF THE INVENTION

The present invention is directed to a novel retractor and a method using such retractor for placing spinal pedicle screws.

SUMMARY OF THE INVENTION

Pedicle screw fixation has become an important part of stabilizing the spine to assist in arthrodesis. Traditionally a significant amount of muscle dissection has been required to prepare for screw placement. Recently, various approaches have been developed to minimize unnecessary disturbance of paraspinous structures while still accomplishing satisfactory fixation of the spine and the concomitant grafting necessary to achieve arthrodesis.

The retractor of the present invention eases intermuscular placement of pedicle screws by providing a minimally invasive approach, and specifically lends itself to image guided applications. The characteristics of the retractor are described below with accompanying figures to illustrate the features.

The retractor's guide channel is of an appropriate length to provide access from the skin surface to the dorsal aspect of the vertebra over the pedicle. The handle of the retractor is attached to provide appropriate holding leverage to maintain the position of the retractor and to stabilize its guide portion against the lateral aspect of the facet with the paraspinous musculature.

An elongated insert may be placed within the guide channel of the retractor. The insert provides a working channel or hollow bore of an appropriate size to accommodate various instruments. For example, the working channel may receive an awl or perforator for the bony cortex, a drill for the pedicle if desired, or a tap for the pedicle and body of the vertebra. The working channel also provides a pathway for a probe or feeler to inspect the placement of the screw. Additionally, the insert may be configured to allow for guided instruments to confirm position of the screw placement. Moreover, attachment of a tracker to the retractor, the insert, or to instruments used through the insert allows coupling of the surgical procedure with an image guided system.

The retractor is configured such that removal of the insert from the guide channel of the retractor provides a protected working channel for placement of the pedicle screw. The tip of the retractor may be textured and obliquely cut to help maintain position of the retractor against the lateral aspect of the facet. The guide channel is preferably open on one side to allow removal of the retractor after placement of the screw. The channel is of sufficient length to maintain muscle retraction necessary for screw placement.

The shape of the distal end of the retractor aids easy placement of the retractor with minimal muscle separation, thus helping to displace soft tissues while placing the retractor and minimizing the tendency of the retractor to catch on soft tissue during entry. Preferably, there are projections and a textured distal surface to help maintain position against the bone and to avoid displacement while working through the retractor. The cutout, preferably semicircular or curved, at the distal end is of an appropriate size to allow use of a tap and subsequent placement of a pedicle screw.

BRIEF DESCRIPTION OF THE DRAWINGS

FIG. 1 is a perspective view of one embodiment of the retractor of the present invention, and front and rear views of an embodiment of the insert for the retractor;

FIG. 1a is an enlarged view of the distal end of the retractor;

FIG. 2 is a front elevation view of the retractor of FIG. 1, taken along arrow 15, of one embodiment of the insert for the retractor adapted for use with a surgical tap, and a surgical tap;

FIG. 3 is a vertical cross-sectional view of the retractor and an insert mounted within the retractor;

FIG. 4 is a horizontal cross-sectional view of the retractor taken along line 4-4 of FIG. 3 and an insert mounted within the retractor;

FIG. 5 is perspective view of the retractor of the present invention during use in a human spine wherein an insert is placed within the retractor and a tap is inserted through the insert;

FIG. 6 is another perspective view of the retractor, with the insert removed and the retractor being used as a guide for emplacement of a pedicle screw;

FIG. 7 is a perspective view of a further embodiment of the present invention having a recessed and curved distal tip at its guide portion; and FIG. 8 is a perspective view of the retractor of the present invention fitted with an image tracker on the retractor's handle, shown in simulated application with the human spine.

DETAILED DESCRIPTION

With reference to FIG. 1, retractor 10 of the present invention is depicted in a perspective view. Retractor 10 preferably comprises two portions, a handle 12 and a guide portion 14. Handle 12 is attached to the proximal end of guide portion 14. Handle 12 may be of various configurations to allow access to the surgical site while providing a means of gripping the retractor 10 such that sufficient leverage may be applied to maintain the desired orientation of retractor 10 at the surgical site. In a preferred embodiment, handle 12 is oriented at an angle of between about 90 and about 135 degrees from the guide portion 14. Handle 12 may include a slot 18 for interconnecting an attachment or a supplemental handle using handle screws 20. Provision of slot 18 allows for various supplemental handle configurations to be used with retractor 10 to provide different holding leverages, as well as to provide interchangeable geometries that may be desired to overcome spatial constraints imposed by a specific patient's physical attributes. Alternately, an image tracker may be attached to slot 18 as discussed further below.

Guide portion 14 is used for access to the interior of the surgical site. Typically, an incision is made in the patient's skin and muscle. Subsequently, the guide portion 14 is inserted through the exterior portion of the incision to create and maintain access to the interior targeted body part, such as the patient's spine. As described below, specific features of guide portion 14 provide for improved access to the spine.

Guide portion 14 is preferably half-cylinder or U-shaped. More particularly, the rear surface 16 of guide portion 14 is preferably convex when viewing retractor 10 from the rear side of retractor 10. The U-shaped front of guide portion 14 includes a hollow region or guide channel 22. Guide channel 22 extends from the distal end 23 of guide portion 14 up to and including the upper-most or proximal end of guide portion 14. In this manner, guide channel 22 may be used to guide surgical tools and implants from the exterior of the surgical site down to the interior-most portion of the surgical site by inserting surgical tools down through the guide channel.

The distal end 23 of guide portion 14 includes a rounded tip 24. In addition, the distal end 23 of guide portion 14 is shown as being truncated obliquely along the lower medial face 25 to more closely approximate the lateral aspect of the facet of the paraspinous musculature of the patient, and provide for improved medial positioning of the guide portion 14 for placement of a drill and/or tap into the bony structure of the patient. The rounded tip 24 may further include a cutout or an opening 26 at its end. In a preferred embodiment shown in FIG. 1a, opening 26 is semicircular. One or more projections 27 may be provided around the end-most portion of opening 26 to aid in maintaining the position of the retractor 10 during use by stabilizing retractor 10 against the bony surface of the vertebrae. In addition, texturing such as ridges and grooves or machined points may be placed on the medial surface 29 of the lower medial face 25 of guide portion 14 to further stabilize retractor 10 when in use.

Referring now also to FIGS. 2 and 4, to aid in facilitating use of tools at the distal end of guide portion 14, an insert 30 may be placed within guide channel 22 to assist the surgeon in guiding and aligning tools along the desired orientation. In a preferred embodiment, insert 30 is generally triangular-shaped and has an aperture or hollow bore 32. Hollow bore 32 allows various tools to be guided down to the targeted area within the surgical site, such as tap 33.

Triangular-shaped insert 30 includes base edges 34. Base edges 34 of insert 30 cooperate with grooves 36 located within guide channel 22 to stabilize insert 30 within guide channel 22. Base edges 34 are simply side projections which mate with the grooves 36. Alternately, in lieu of base edges 34, insert 30 may include one or more discontinuous side projections (not shown). Similar to the base edges 34 of insert 30, these side projections could cooperate with a corresponding number of discontinuous grooves (not shown) located within guide channel 22 to aid in stabilizing insert 30 within guide channel 22.

Insert 30 includes a distal tip 38, a longitudinal shaft 40, a proximal end 42, and an optional handle 43. The distal tip 38 of insert 30 may be rounded, defining a perimeter edge 44. Perimeter edge 44 cooperates with the lower distal portion of groove 36 within guide channel 22 to further stabilize the distal tip 38 of insert 30, and to further prevent unnecessary entanglement with the patient's bodily tissues when inserting the insert 30 into the guide channel 22.

Referring now to FIGS. 3 and 4, the retractor 10 of the present invention is shown with insert 30 received in the retractor 10. As described above, the base edges 34 of the triangular-shaped insert 30 mate with corresponding grooves 36 in the guide channel 22 of retractor 10. The distal tip 38 of insert 30 mates with the distal end 23 and rounded tip 24 of retractor guide portion 14 such that insert 30 does not extend beyond distal end 23. FIGS. 3 and 4 also depict the hollow bore 32 through which a drill or tap 33 is inserted, thereby guiding the tap 33 to its targeted location.

With reference to FIG. 5, a tap 33 is shown inserted though the bore 32 of the insert 30, and the insert is placed in the guide channel 22 of retractor 10. Tap 33 is used to create an appropriate bore in the bone "B" for receipt of a medical device, such as a pedicle screw "S". Tap 33 may be sized in diameter to restrict passage of the tap 33 beyond a specified length through insert 30. Specifically, tap 33 may contain a larger diameter section 50 which prevents passage of the tap 33 beyond the proximal opening 42 of insert 30.

With reference now to FIG. 6, once the tapping operation is complete, tap 33 and insert 30 may be removed from guide channel 22. Guide channel 22 remains in place and is then used to guide a medical device, in this case, a pedicle screw S. The retractor 10 thus provides for proper alignment of the screw S. Further, the opening 26 in the distal end 23 of guide channel 22 is sized and shaped to accommodate the shank of screw S so that screw S may be properly aligned with the bore created by tap 33. Tool T, such as a medical screwdriver, is then used to finish installation of screw S by screwing screw S into bone B.

Referring now to FIG. 7, in a further embodiment, a retractor 10' without a rounded tip is illustrated. As shown, the retractor has a recessed and curved distal tip 54. This embodiment offers the advantage of offering a U-shaped guide channel 22; however, a rounded tip is not present to interfere with visibility of the surgical site. The U-shaped guide channel 22 extends from the upper end of guide portion 14 down to the distal end 23 of the guide portion 14. As with the previous embodiment, distal end 23 of the guide portion 14 may be obliquely cut, with optional projections (not shown) formed at the end-most portion of the distal end 23. Additional texturing may also be provided along the medial surface of guide portion 14 to assist with stabilizing retractor 10' against the neighboring area of the surgical site.

Due to the frequently limited amount of exposure of the spine or interior surgical area, the spinal implant procedures lend themselves to use of image guidance for surgery. Examples of such image guidance systems include the BrainLAB System and the Stealth System. As understood by those skilled in the art, these image guidance systems utilize a computer system with a monitor and two cameras that emit infrared signals, thereby determining the patient's position in the operating room as well as the position of the surgical instruments in relation to the patient's spine. The image guidance systems use data from standard CT or MRI scans to build a three dimensional image of the patient's spine. This model is then electronically matched to the patient's anatomy during surgery, allowing the surgeon, in effect, to see through tissue in order to accurately determine the placement of instruments or devices. During the operation, sensitive structures such as blood vessels and nerves, which the surgeon wants to avoid on the way to the anatomical target, can be visualized. In addition, during the operation the surgeon can follow the movements of his or her instruments on the computer screen in real time.

Referring now to FIG. 8, retractor 10 is shown in one possible relationship with the human spine. The retractor 10 can be positioned at a desired location in relation to spinal processes and maintained in position with the projections 27 and texturing 28 which assist in anchoring the retractor on the patient. The insert 30 may then be used as a guide for subsequent tapping, or like operations. The retractor 10 with insert 30 provides a working channel for tracked instruments. Attachment of a tracker 60 directly to insert 30, or alternately to the retractor handle 12 as shown in FIG. 8, allows a surgeon to guide the guide channel 22 of retractor 10, or hollow bore 32 of insert 30 directly, and thus avoid tracking the instruments themselves, such as a drill or tap 33.

All components of the invention described herein are manufactured of a material appropriate for surgical use. For example, the components can be made of stainless steel. However, it is to be understood that other types of materials may also be used, such as titanium or ceramics.

While various embodiments of the present invention have been described in detail, it is apparent that modifications and adaptations of those embodiments will occur to those skilled in the art. However, it is to be expressly understood that such modifications and adaptations are within the spirit and scope of the present invention.

What is claimed is:

1. A retractor especially adapted for placement of a pedicle screw within a patient, comprising:
    a guide portion having a guide channel extending longitudinally therealong, said guide portion having a first and second end, and a medial face positioned adjacent said second end thereof, said medial face having a medial surface formed with texturing thereon;
    a handle connected angularly with respect to said first end of said guide portion; and
    an insert configured to fit within said guide channel, said insert having an aperture extending lengthwise therethrough, said aperture having a diameter sized to accommodate a tool being inserted therethrough.

2. The retractor as claimed in claim 1, further comprising means for stabilizing said refractor against a lateral aspect of a facet of a paraspinous musculature of the patient.

3. The retractor as claimed in claim 1, wherein said texturing comprises at least one projection extending from said second end of said guide portion for assisting in anchoring the guide portion within the surgical area.

4. The retractor as claimed in claim 2, wherein said means comprises an obliquely truncated portion formed along the medial face of the guide portion.

5. The retractor as claimed in claim 1, further comprising grooves formed within said guide channel for receiving at least one base edge of said insert.

6. The retractor as claimed in claim 1, further comprising an image tracker mounted to said retractor.

7. The retractor as claimed in claim 1, wherein the guide portion is adapted to be stabilized against a lateral aspect of a facet of a paraspinous musculature of the patient.

8. The retractor as claimed in claim 7, wherein the guide portion includes an obliquely truncated portion formed along the medial face thereof.

9. A retractor for placement of a pedicle screw, comprising:
    a guide portion including a guide channel;
    an insert configured to fit within said guide channel, said insert having a hollow bore extending lengthwise therethrough, said bore having a diameter sized to accommodate a tool inserted therethrough; and
    grooves formed within said guide channel for stabilizing said insert within said guide channel.

10. The retractor as claimed in claim 9, wherein said guide channel includes a distal end, said distal end having at least one projection extending therefrom.

11. The retractor as claimed in claim 9, wherein said guide portion includes a medial face positioned adjacent said second end thereof, said medial face having a medial surface formed with texturing thereon.

12. The retractor as claimed in claim 9, further comprising an image tracker mounted to said refractor.

13. A surgical retractor for guiding implantation of a pedicle screw within a patient's spine, comprising:
    a guide portion having a guide channel, said guide channel sized to accommodate a pedicle screw for implanting in the patient, said guide portion having a distal end and a semi-circular opening sized to accommodate a pedicle screw at said distal end of said guide portion; and
    means for stabilizing the distal end of said guide portion against a lateral aspect of a facet of a paraspinous musculature of the patient.

14. The retractor as claimed in claim 9, further comprising an elongated insert configured to fit within said guide channel, said insert having an aperture extending lengthwise therethrough.

15. The retractor as claimed in claim 14, further comprising grooves formed on said guide channel for receiving at least one base edge of said insert.

16. The retractor as claimed in claim 13, further comprising an image tracker mounted to said retractor.

17. In combination, a retractor especially adapted for spinal surgery and an image tracker, said combination comprising:
    a retractor having a guide portion and a guide channel portion extending longitudinally therealong;
    a handle connected to said guide portion;
    an insert configured to fit within said guide channel and having an aperture extending lengthwise therethrough; and
    an image tracker connected to said insert, wherein the image tracker allows the aperture to be aligned on the surgical site.

18. The combination as claimed in claim 17, wherein the aperture in the insert is configured to receive a tap.

19. The combination as claimed in claim 18, wherein said insert includes a proximal opening sized to prevent a larger diameter section of said tap from passing into said aperture.

20. A method for placing a pedicle screw, comprising:
    providing a refractor including a guide portion having first and second ends, said guide portion including a guide channel, said guide portion having a handle operatively connected thereto;
    placing said guide portion so as to extend from a skin surface of a patient to a dorsal aspect of a vertebra over a pedicle of said patient;
    manipulating said handle so as to maintain a position of said guide portion against a lateral aspect of a facet of a paraspinous musculature of said patient;
    inserting an insert into said channel of said retractor, said insert having a hollow bore sized to accommodate a tool selected from the group consisting of a drill bit, a tap for a pedicle and a probe;
    utilizing the tool to complete a desired surgical step within a surgical procedure;
    removing said insert after utilizing said tool; and
    inserting a pedicle screw into said pedicle.

21. A method for placing a bone screw in a vertebra, the method comprising:
    placing a retractor through a skin incision, the retractor including a guide channel having a proximal end and a distal end,
    advancing the distal end of the guide channel into contact with a vertebra, the guide channel extending from the skin incision to the vertebra, and
    advancing a pedicle screw along the guide channel and into engagement with the vertebra.

22. The method of claim 21, further comprising inserting an insert into the guide channel.

23. The method of claim 22, the insert is inserted before placing the retractor through the skin incision.

24. The method of claim 22, wherein the insert is inserted after placing the retractor through the skin incision.

25. The method of claim 22, further comprising advancing a tool through the insert to the vertebra.

26. The method of claim 25, further comprising creating an opening in the vertebra for the bone screw utilizing the tool.

27. The method of claim 21, further comprising maintaining the distal end of the guide channel in contact with the vertebrae during advancement of the pedicle screw along the guide channel.

28. The method of claim 21, further comprising advancing a tool along the guide channel.

29. The method of claim 28, wherein the tool is advanced along an insert positioned in the channel.

30. The method of claim 28, creating an opening in the vertebra for the bone screw utilizing the tool.

31. A method for placing a bone screw in a vertebra, the method comprising:
  making an incision in the skin of a patient;
  creating a pathway from the incision to proximate a vertebra;
  placing a retractor through the incision, the retractor including a guide channel having a proximal end and a distal end;
  advancing the distal end of the guide channel into contact with a vertebra, the guide channel extending from the incision to the vertebra;
  manipulating the retractor to maintain the pathway to the vertebra; and
  advancing a pedicle screw along the guide channel and into engagement with the vertebra.

* * * * *